United States Patent [19]

Hyde et al.

[11] Patent Number: 5,755,765
[45] Date of Patent: May 26, 1998

[54] PACING LEAD HAVING DETACHABLE POSITIONING MEMBER

[75] Inventors: Gregory M. Hyde, Sunnyvale, Calif.; Stuart R. Chastain, Shoreview, Minn.; Bruce A. Tockman, Scandia, Minn.; Randy W. Westlund, Minneapolis, Minn.; Ronald W. Heil, Jr., Roseville, Minn.; David M. Flynn, Lino Lakes, Minn.; Randall M. Peterfeso, St. Paul, Minn.

[73] Assignee: Cardiac Pacemakers, Inc., St. Paul, Minn.

[21] Appl. No.: 787,287

[22] Filed: Jan. 24, 1997

[51] Int. Cl.⁶ .................... A61N 1/05; A61N 1/04
[52] U.S. Cl. .................... 607/122; 607/119; 607/125
[58] Field of Search .................... 607/119, 122, 607/125

[56] References Cited

U.S. PATENT DOCUMENTS

| | | |
|---|---|---|
| 4,932,407 | 6/1990 | Williams . |
| 5,014,696 | 5/1991 | Mehra . |
| 5,099,838 | 3/1992 | Bardy . |
| 5,304,218 | 4/1994 | Alferness .................... 607/122 |
| 5,348,021 | 9/1994 | Adams et al. . |
| 5,350,404 | 9/1994 | Adams et al. . |
| 5,381,790 | 1/1995 | Kanesaka .................... 607/125 |
| 5,433,729 | 7/1995 | Adams et al. . |
| 5,458,621 | 10/1995 | White et al. . |
| 5,545,204 | 8/1996 | Cammilli et al. . |
| 5,687,723 | 11/1997 | Avitall . |

FOREIGN PATENT DOCUMENTS 2032278  5/1980  United Kingdom .................... 607/122

*Primary Examiner*—William E. Kamm
*Assistant Examiner*—Carl H. Layno
*Attorney, Agent, or Firm*—Haugen and Nikolai, P.A.

[57] ABSTRACT

Intravenous cardiac leads having at least one electrode intended to be implanted within the coronary veins are disclosed. Also disclosed are structures and techniques for advancing such leads through the atrium and coronary sinus into the coronary veins.

13 Claims, 3 Drawing Sheets

PACING LEAD HAVING DETACHABLE POSITIONING MEMBER

BACKGROUND OF THE INVENTION

I. Field of the Invention

This invention relates to cardiac leads used in combination with a cardiac rhythm management device, e.g., heart pacemakers or defibrillators, to monitor and control the rhythm of the heart. This invention is more particularly directed toward lead configurations adapted to be implanted in the coronary veins on the left side of the heart and to methods for implanting such leads.

II. Discussion of the Prior Art

As explained in U.S. Pat. No. 4,928,688 to Morton M. Mower dated May 29, 1990, under normal circumstances impulses from the SA node affect contraction of the atria and then propagate to the AV node. The AV node then emits a second nerve impulse which affects contraction of the ventricles. In healthy individuals this is done in a coordinated manner to circulate blood through the body. However, many patients suffer from conditions which inhibit the transfer of nerve impulses from the SA node to the AV node and from there to the ventricles. In such cases, the chambers of the heart do not contract in a coordinated fashion and hemodynamic efficiency of the heart is decreased. This has profound adverse implications for the health and well-being of the patient. In minor cases, the quality of life is considerably reduced. More severe cases can result in death.

The Mower 4,928,688 patent describes a method for improving the hemodynamic efficiency of a sick heart. The method proposed in that patent is to place electrodes in both the right and left ventricles, monitor the cardiac signals originating in the right and left ventricles, analyze these signals and the absence thereof in a control circuit, and provide stimulating pulses to one or both ventricles within a time interval designed to improve the heart's hemodynamic efficiency.

Others have discussed the advantages of implanting leads in both the right and left ventricles to permit a sick heart to be more effectively defibrillated. See, for example, U.S. Pat. No. 4,922,407 to Williams; U.S. Pat. No. 5,099,838 to Bardy; and U.S. Pat. Nos. 5,348,021, 5,433,729, and 5,350,404 all to Adams et al. Each of the patents describe inserting a lead through the right atrium and coronary sinus into one of the coronary veins. None of these patents, however, discuss the difficulties encountered in doing so.

Important health advantages are achieved by positioning an electrode in a branch of the great vein of the heart. A lead so positioned can be used to stimulate the left ventricle. While it would be possible to position the electrode within the left ventricle, this can increase the potential for clot formation. If such a clot were released to the brain, the situation could be life threatening. Yet traditional lead designs are not well suited for implantation in the coronary veins. Traditional lead designs are typically too big, often have some type of fixation device (such as tines or screw types) that must be modified, or are positioned using a stylet which is too stiff.

An arrangement intended to address such difficulties associated with the implantation of leads is disclosed in U.S. Pat. No. 5,304,218 granted to Clifton A. Alferness on Apr. 19, 1994. The arrangement disclosed in this patent includes a lead having an electrode. The electrode has a follower means for slidably engaging a guide wire. The electrode is implanted by feeding the guide wire along the desired path, engaging the follower means to the guide wire, advancing the lead along the guide wire until the electrode resides at the implant site, and retracting the guide wire from the follower means after the electrode is implanted at the implant site.

A review of the specification and drawings of U.S. Pat. No. 5,304,218 and an understanding of the anatomy and physiology of the heart demonstrates several problems with this approach. First, the path through which the lead must be fed is very restricted. The increased size of the distal end of the lead, given the presence of the follower, may make it more difficult to advance such a lead along the desired path so as to be positioned on myocardial tissue of the left ventricle. Second, the direction of blood flow through the veins tends to force electrodes implanted there out of the vein. This problem is likely to be exacerbated by the increase in the profile of the distal end given the presence of the follower. Third, the profile of the distal end of a lead implanted in a coronary vein may need to be made as small as possible to limit occlusion and permit blood to flow as freely as possible through the blood vessel when the lead is in place and to limit damage to the vessels and myocardium.

SUMMARY OF THE INVENTION

The present invention provides an improved lead for implantation of an electrode into a coronary vein on the left side of the heart. The lead includes an elongated, flexible body member made of an electrically insulative material. The body member includes a proximal end and a distal end. A lumen extends through the body member from the proximal end toward the distal end. The lead also includes a conductive member extending through the body member from the proximal end toward the distal end. Electrically coupled to the conductive member near its distal end is an electrode. Additional lumens, electrodes and conductive members may be included within and on the lead body.

Leads made in conformance with the present invention can be inserted in a number of different ways. For example, a guide catheter can be inserted and then the lead passed through the guide catheter until it is properly positioned. Leads can have a lubricious coating to reduce friction. The guide catheter can then be retracted. Similarly, a guide wire can be advanced to the implant site. Using a guide loop near the tip of the lead, the lead can be slid over the guide wire until the electrode is properly positioned. The guide wire can then be retracted. After some period of time, the guide loop will be dissolved by body fluids. Also, the lead can be temporarily fixed to a guide wire using a fixator which is dissolved by body fluids. The lead is then inserted along with the guide wire. After the electrode is in place and the fixator dissolves, the guide wire can be retracted.

Alternative embodiments of the present invention offer other advantages and features. Additional lumens can be provided and the cross-section of the body member can be modified to provide a channel for a guide wire or stylet. The stylet can be used to push against a mechanical stop or reduced internal lumen diameter to advance the lead. These features are shown in the drawings and discussed in further detail below.

DETAILED DESCRIPTION OF THE INVENTION

Figure 1:
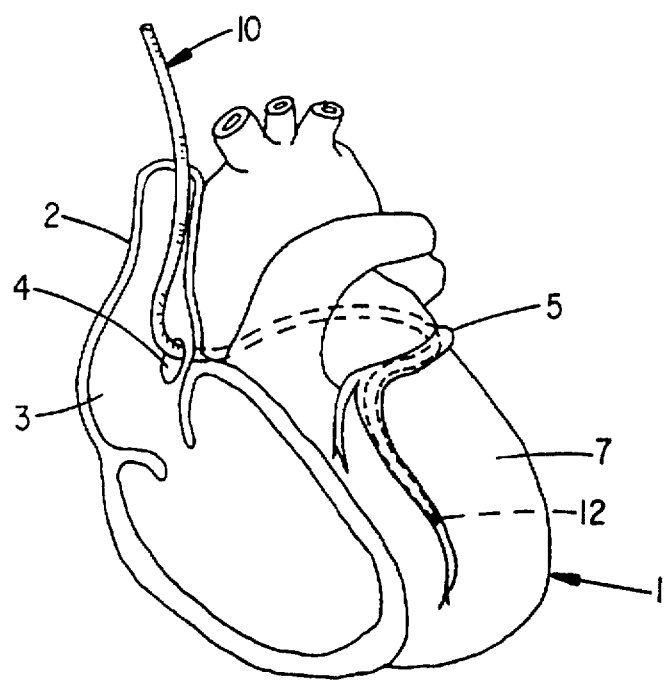
FIG. 1 is a plan view of an intravenous cardiac lead having an electrode positioned in a coronary vein.

FIG. 1 shows a human heart 1 with the intravenous coronary lead 10 of the present invention passing through the superior vena cava 2, the right atrium 3, and the coronary sinus 4 into the great vein of the heart 5 so that an electrode 12 on the lead 10 is implanted in a branch of the coronary vein. When positioned as shown, the electrode 12 can be used to sense the electrical activity of the heart or to apply a stimulating pulse to the left ventricle 7 and without the need of being in the left ventricular chamber.

Figure 2:
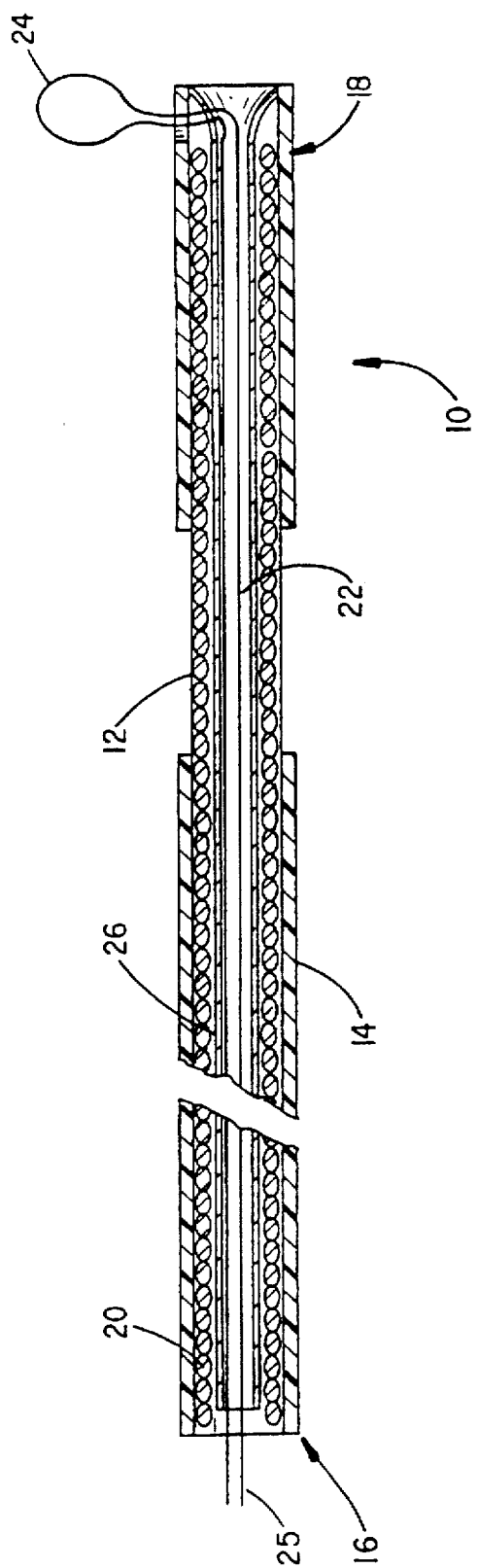
FIG. 2 is a cross-section of a distal end portion of the intravenous cardiac lead shown in FIG. 1.

FIG. 2 shows in greater detail the structure of the intravenous coronary lead shown in FIG. 1. As shown in FIG. 2, the lead 10 includes an elongated body member 14 having a proximal end 16 and a distal end 18. The body member 14 is preferably made of a flexible, electrically insulative material. The outer surface of the body member 14 is preferably treated to prevent fibrotic attachment and to reduce inflammation response to the lead. Such a treatment could include a carbon coating, a steroid embedded in the material, a steroid eluting collar, or the like.

The body member 14 encapsulates a flexible electrically conductive member 20 extending from the proximal end 16 toward the distal end 18 of the lead's body member 14. Conductive member 20 is shown as a flexible wire coil in FIG. 2. Alternatively, the conductor member 20 could be in the form of a conductive wire, a thin ribbon, a plurality of fine wires formed as a cable, or a flexible tube without deviating from the invention.

FIG. 2 also shows the lead 10 as including a central lumen 22 extending from the proximal end 16 to the distal end 18 of the body member 14. The lumen can be used to insert a guide wire and a stylet to add stiffness and to push the lead forward.

The electrode 12 shown in FIG. 2 is preferably created by removing an annular portion of the insulative body member 14 to expose a portion of the underlying conductive member 20. When the conductive member 20 is a coil as shown in FIG. 2, the turns of the coil can be melt-banded such as by application of laser energy, to form the surface electrode 12. Those skilled in the art will recognize that a ring electrode electrically coupled to the conductive member 20 will also suffice. The electrode 12 can be positioned at various points along the body member 14. Additional ring electrodes and tip electrodes can also be placed on the body member 14. When each is coupled to its own conductive member, the individual electrodes can be used for sensing, pacing or defibrillating.

One or more loops such as the loop 24 shown in FIG. 2 can be used to guide the lead over a guide wire. A surgeon can advance a guide wire through the coronary sinus veins to the proper position for the electrode 12. The free end of the guide wire can then be inserted through the loop 24 near the distal end 18 and the lead 10 slid alongside the guide wire to position the electrode 12 by pushing with a stylet (not shown) inside the lead. The guide wire can then be retracted through the loop 24.

The loop 24 can be formed in several ways. For example, it can be formed of a material which is dissolved by body fluids over time. Alternatively, it can be a permanent fixture of the lead. It can also be temporarily fixed to the lead body 14 using a dissolvable material such as mannitol and attached to or formed integrally with one or more cords 25 which run the length of the lead through a lumen. The cords 25 can then be used to retract the loop 24 through the lumen after the fixing material has dissolved. Either the lumen, the outer surface of the body member, or both can be coated with a lubricious material to ease insertion or retraction.

Figure 3:
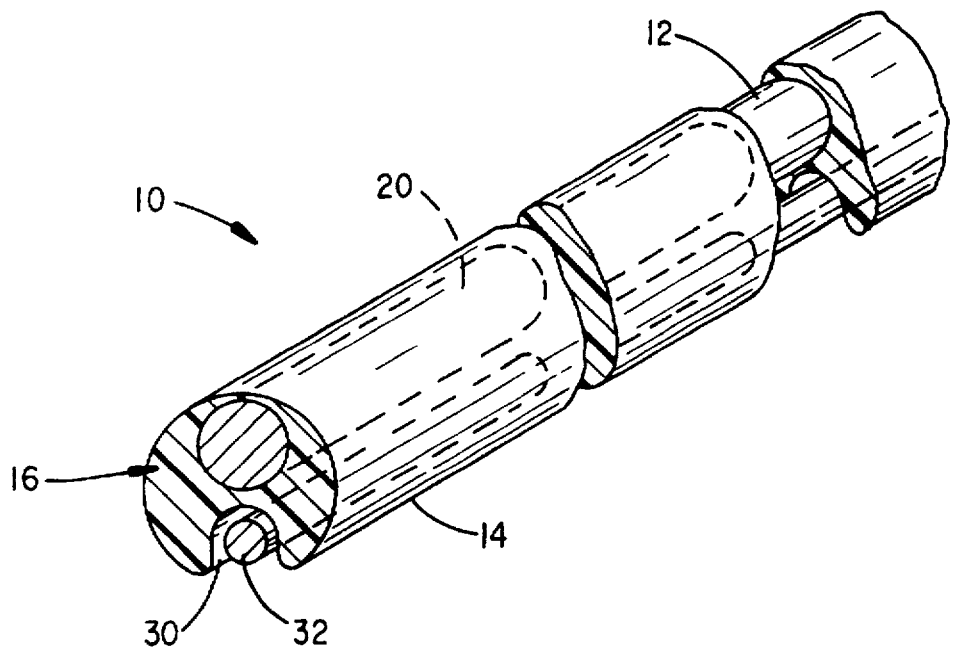
FIG. 3 is a perspective view of an alternative embodiment of the intravenous cardiac lead.
Figure 4:
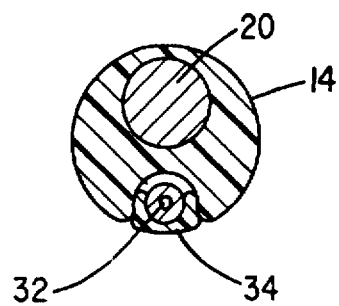
FIG. 4 is a transverse cross-section through line 44 in FIG. 3.

FIGS. 3 and 4 show an alternative embodiment of the invention. In this embodiment, the lead 10 has an electrode 12, body member 14, and a conductive member 20. The conductive member 20 can be in the form of a highly flexible conductive cable as shown. It can also be a coil as shown in FIG. 2, a tube or a wire. In the embodiment shown in FIGS. 3 and 4, the body member 14 includes a lumen 30 in the form of an open channel extending from the proximal end 16 toward the distal end 18. The lumen 30 is designed to received a guide wire 32. As shown in FIG. 4, the guide wire 32 may be fixed to the lumen 30 with a fixing material 34 such as mannitol or some other dissolvable material. This arrangement permits the lead 10 and guide wire 32 to act as one as the lead 10 is advanced. Body fluids will quickly dissolve the fixing material 34 allowing the guide wire 32 to be separated from the lumen 30 and retracted from the patient.

While not shown in any of the views, each lead will have one or more connectors of a type known in the art at its proximal end for mating with the pacer and/or defibrillator pulse generator whereby depolarization signals originating in the heart can be sensed and stimulating pulses applied in accordance with the device's control algorithms.

The foregoing discussion is intended to illustrate various preferred arrangements for meeting the objections of the present invention. Modifications and variation can be made by those skilled in the art without departing from the invention. Accordingly, the invention is limited only by the scope of the following claims which are intended to cover all alternate embodiments and modifications as may fall within the true scope of this invention.

What is claimed:

1. For use with a cardiac rhythm management device, an intravenous lead having:
   (a) an elongated, flexible body member made of an electrically insulative material, said body member having an outer surface, a proximal end and a distal end;
   (b) an electrode coupled to said body member;
   (c) an electrically conductive member coupled to said electrode; and
   (d) means for fixing said body member to a positioning member, said positioning member comprising a guide catheter.

2. For use with a cardiac rhythm management device, an intravenous lead having:
   (a) an elongated, flexible body member made of an electrically insulative material, said body member having an outer surface, a proximal end and a distal end;
   (b) an electrode coupled to said body member;
   (c) an electrically conductive member coupled to said electrode; and
   (d) means dissolvable by body fluids for releasably fixing said body member to a positioning member.

3. The lead of claim 2 wherein said body member has a channel for receiving at least a portion of said positioning member and the means for fixing said body member to said positioning member holds a portion of said positioning member in said channel until said means for fixing is dissolved by body fluids.

4. The lead as in claim 1 wherein the means for fixing said body member to a positioning member comprises a loop near the distal end of the flexible body member.

5. The lead of claim 2 further including at least one lumen extending from the proximal end toward the distal end and an electrically conductive member running from said electrode through said lumen toward the proximal end of the elongated flexible body member.

6. The lead of claim 5 wherein at least a portion of at least one of said lumens is treated with a lubricious material.

7. The lead of claim 5 wherein a guide wire is insertable through one of said lumens.

8. The lead of claim 5 wherein a stylet is insertable through one of said lumens.

9. The lead of claim 5 wherein a stylet and guide wire are insertable through said lumens.

10. The lead of claim 1 or claim 2 further including a coating on said outer surface of said elongated flexible body member which prevents fibrotic attachment and reduces inflammation response.

11. The lead of claim 1 or claim 2 further including a coating on at least a portion of said outer surface of said elongated flexible body made of a lubricious material.

12. The lead of claim 1 or 2 wherein said body member is treated with an anti-inflammatory agent.

13. The lead of claim 1 or 2 wherein said lead body member is treated with an antifibrotic agent.

* * * * *